United States Patent [19]

Wallner et al.

[11] Patent Number: 5,185,441

[45] Date of Patent: Feb. 9, 1993

[54] DNA SEQUENCES, RECOMBINANT DNA MOLECULES AND PROCESSES FOR PRODUCING PI-LINKED LYMPHOCYTE FUNCTION ASSOCIATED ANTIGEN-3

[75] Inventors: Barbara P. Wallner, Cambridge; Catherine Hession, South Weymouth, both of Mass.

[73] Assignee: Biogen, Inc., Cambridge, Mass.

[21] Appl. No.: 237,309

[22] Filed: Aug. 26, 1988

[51] Int. Cl.[5] .................... C07H 21/00; C07H 21/04; C12Q 1/68

[52] U.S. Cl. ..................... 536/23.5; 435/6; 435/90; 435/172.3.69.3; 435/252.34; 435/252.21; 435/240.1; 435/320.1; 436/501; 935/6; 935/19; 935/29; 935/78; 935/88; 935/77

[58] Field of Search ............ 435/6, 91, 69.3, 172.3; 436/501; 536/27; 935/6, 19, 29, 77, 78, 88

[56] References Cited

U.S. PATENT DOCUMENTS

4,738,927 4/1988 Taniguchi et al. .................. 435/243
4,956,281 9/1990 Wallner et al. ..................... 435/69.3

FOREIGN PATENT DOCUMENTS

8806592 9/1988 PCT Int'l Appl. .
8809820 12/1988 PCT Int'l Appl. .

OTHER PUBLICATIONS

Barthels et al., "Isolation and Nucleotide Sequence of Mouse NCAM cDNA that Codes for a M,79000 Polypeptide Without a Membrane-Spanning Region," *EMBO Journal*, 6 (4), pp. 907–914 (1987).

Benton et al., "Screening λgt Recombinant Clones by Hydridization to Single Plaques in situ," *Science*, 196, pp. 180–182 (1977).

Cate et al., "Isolation of the Bovine and Human Genes for Mullerian Inhibiting Substance and Expression of the Human Gene in Animal Cells," *Cell*, 45, pp. 685–698 (1986).

Church and Gilbert, "Genomic Sequencing", *Proc. Natl. Acad. Sci. U.S.A.*, 81, pp. 1991–1995 (1984).

Cunningham et al., "Neural Cell Adhesion Molecule: Structure, Immunoglobulin-Like Domains, Cell Surface Modulation, and Alternative RNA Splicing," *Science*, 236, pp. 799–806 (1987).

Dustin et al., "Purified Lymphocyte Function-Associated Antigen-3 Binds to CD2 and Mediates T Lymphocyte Adhesion," *J. Exp. Med.*, 165, pp. 677–692 (1987) [Dustin et al. I].

Dustin et al., "Anchoring Mechanisms for LFA-3 Cell Adhesion Glycoprotein at Membrane Surface," *Nature*, 329, pp. 846–848 (1987).

Grosveld et al., "the Construction of Cosmid Libraries Which Can be Used to Transform Eukaryotic Cells", *Nucleic Acids Research*, 10, pp. 6715–6732 (1982).

Gubler et al., "A Simple and Very Efficient Method for Generating cDNA Libraries," *Gene*, 25, pp. 263–269 (1983).

Hawkes et al., "A Dot-Immunobinding Assay for Monoclonal and Other Antibodies," *Anal. Biochem.*, 119, 142–147 (1982).

He et al., "Phosphatidylinositol is Involved in the Membrane Attachment of NCAM-120, the Smallest Component of the Neural Cell Adhesion Molecule," *EMBO Journal*, 5, (10), pp. 2489–2494 (1986).

Hewick et al., "A Gas-Liquid Solid Phase Peptide and Protein Sequentor," *J. Bio. Chem.*, 256, 7990–7997 (1981).

Kranz et al., "Immunoprecipitation of Cell Surface of Cloned Cytotoxic T Lymphocytes by Clone-Specific Antisera," *Proc. Natl. Acad. Sci. U.S.A.*, 81, pp. 573–577 (1984).

(List continued on next page.)

Primary Examiner—Margaret Moskowitz
Assistant Examiner—Ardin H. Marschel
Attorney, Agent, or Firm—James F. Haley, Jr.; Denise L. Loring; Immac J. Thampoe

[57] ABSTRACT

Polypeptides that bind to CD2, the receptor on the surface of T-lymphocytes. Most preferably, the polypeptides are soluble. DNA sequences that code on expression and/or secretion in appropriate unicellular hosts for those polypeptides.

15 Claims, 6 Drawing Sheets

OTHER PUBLICATIONS

Lai et al., "Two Forms of TB236/Myelin-Associated Glyco Protein, a Cell Adhesion Molecule for Postnatal Neural Development, are Produced by Alternative Splicing," *Proc. Natl. Acad. Sci. U.S.A.*, 84, pp. 4337–4441 (1987).

Low, "Biochemistry of the Glycosyl-Phosphatidylinositol Membrane Protein Anchors," *Biochem. J.*, 244, pp. 1–13 (1987).

Maniatis et al., "Extraction, Purification, and Analysis of mRNA from Eukaryotic Cells," *Molecular Cloning*, pp. 187–209 (Cold Spring Harbor Lab 1982).

March et al., "A Simplified Method for Cyanogen Bromide Activation of Agarose for Affinity Chromatography," *Anal. Biochem.*, 60, pp. 149–152 (1974).

Makgoba et al., "Human T Cell Rosetting is Mediated by LFA-3 on Autologous Erythrocytes," *J. of Immunol.*, 138, pp. 3587–3589 (1987).

Maxam and Gilbert, "A New Method for Sequencing DNA," *Proc. Natl. Acad. Sci. U.S.A.*, 74, pp. 560–564 (1977).

Maxan and Gilbert, "Sequencing End-Labled DNA with Base-Specific Chemical Cleavages," *Meth. Enzymol.*, 65, pp. 499–560 (1980).

Mulligan et al., "Selection for Animal Cells that Express the Escherichia Coli Gene Coding for Xanthine-Guanine Phophoribosyltransferase," *Proc. Natl. Acad. Sci. U.S.A.*, 78, pp. 2072–2076 (1981).

Okayama et al., "High-Efficiency Cloning of Full-Length cDNA," *Mol. Cell. Biol.*, 2, pp. 161–170 (1982).

Pepinsky et al., "Purification and Partial Sequence Analysis of a 37-kDA Protein that Inhibits Phospholipase $A_2$ Activity from Rat Periotoneal Exudates," *J. Bio. Chem.*, 261, 4239–4246 (1986).

Sanchez-Madrid et al., "Three Distinct Antigens Associated with Human T-Lymphocyte-Mediated Cytolysis: LFA-1, LFA-2, and LFA-3," *Proc. Natl. Acad. Sci. U.S.A.*, 79, pp. 7489–7493 (1982).

Seed et al., "An LFA-3 cDNA Encodes a Phospholipid Linked Membrane Protein Homologous to its Receptor CD2," *Nature*, 329, pp. 840–842 (1987).

Selvaraj et al., "Deficiency of Lymphocyte Function Associated Antigen 3 (LFA3) in Paroxysmal Nocutrnal Hemoglobinuria," *J. Exp. Med.*, 166, pp. 1011–1025 (1987).

Sewell et al., "Molecular Cloning of the Human T-Lymphocyte Surface CD2 (T11) Antigen," *Proc. National Acad. Sci. U.S.A.*, 83, pp. 8718–8722 (1986).

Southern E. M., "Detection of Specific Sequences Among DNA Fragments Separated by Gel Electrophoresis," *J. Mol. Biol.*, 98, pp. 503–517 (1975).

Springer et al., "The Lymphocyte Function-Associated LFA-1, CD2, and LFA-3 Molecules: Cell Adhesion Receptors of the Immune System," *Ann. Rev. Immunol.*, 5, pp. 223–232 (1987).

Wallner et al., "Cloning and Expression of Human Lipocortin, a Phospholipase A2 Inhibitor with Potential Anti-Inflammatory Activity," *Nature*, 320, pp. 77–81 (1986).

Wallner et al., "Primary Structure of Lymphocyte Function-Associated Antigen 3 (LFA-3)," *J. Exp. Med.*, 166, pp. 923–932 (1987).

Wong et al., "Identification of a Partial cDNA Clone for the Human Receptor for Completement Fragments C3b/C4b," *Proc. Natl. Acad. Sci. U.S.A.*, 82, 7711–7715 (1985).

Conzelmann et al. (1986) EMBO J., vol. 5, No. 12, pp. 3291–3296.

Ferguson et al. (1988) Ann. Rev. Biochem., vol. 57, pp. 285–320.

Hyman (1985) Biochem J., vol. 225, pp. 27–40.

FIG. 1

| | | |
|---|---|---|
| NH₂ Terminus LFA-3 | : | FS<u>QQ</u>IYG<u>VV</u>YGXVTFHVPSNVP LKEVL<u>WKKQKDK</u>VAEL |
| T₇₂₋₇₃ | : | DKVAELENSEF |
| T₉₁ | : | VYLDTVSGSLTIYNLTS |
| T₁₀₅ | : | FFLYVLESLPSPTLTCAL |
| T₆₈ | : | GLIMYS |

FIG. 5

| | | |
|---|---|---|
| LF-10 | : | cgtcgctcccagcaaccatggctcgtcggg |
| LF-11 | : | catggaaagttacattcccatacacaacacc |
| NN-A | : | gatcctcacatcccaatccg |
| NN-B | : | tccaaccaccaatctcaaag |
| NN-C | : | cggattgggatgtgaggatc |
| NN-D | : | ctttgagattggtggttgga |

Oligonucleotide Probe Pool LF1:

20mer, 32 fold degenerate

FIG. 2

Corresponds to amino acid sequence:

```
         trp  lys  lys  gln  lys  asp  lys
    5'   TGG  AAA  AAA  CAG  AAA  GAC  AAA
              G    G    A    G    T    G
```

Probe Sequence:
```
    3'   ACC  TTT  TTT  GTC  TTT  CTG  TT
              C    C    T    C    A
```

Oligonucleotide Probe Pool LF2-5:

20mer 384 fold degenerate. Synthesized in four subpools of 96fold degeneracy.

Correspond to amino acid sequence:

```
         gln  gln  ile  tyr  gly  val  val
    5'   CAG  CAG  ATC  TAC  GGN  GTN  GTN
              A    A    T    T
                             A
```

Probe Sequence:
```
    3'   GTC  GTC  TAG  ATG  CCN  CAN  CA
              T    T    A    A
                             T LF2: 3'  GTC  GTC  TAG  ATG  CCA  CAN  CA
              T    T    A    A
                             T LF3: 3'  GTC  GTC  TAG  ATG  CCT  CAN  CA
              T    T    A    A
                             T LF4: 3'  GTC  GTC  TAG  ATG  CCG  CAN  CA
              T    T    A    A
                             T LF5: 3'  GTC  GTC  TAG  ATG  CCC  CAN  CA
              T    T    A    A
                             T
```

FIG. 3

P24 AMINO ACID AND cDNA SEQUENCES

```
  1 GCGGCCGCCGACGAGCCATGGTTGCTGGGAGCGACGCGGGGCGGGCCCTG  50
                   MetValAlaGlySerAspAlaGlyArgAlaLeu
                   -28
 51 GGGGTCCTCAGCGTGGTCTGCCTGCTGCACTGCTTTGGTTTCATCAGCTG 100
    GlyValLeuSerValValCysLeuLeuHisCysPheGlyPheIleSerCy
101 TTTTTCCCAACAAATATATGGTGTTGTGTATGGAATGTAACTTTCCATG  150
    sPheSerGlnGlnIleTyrGlyValValTyrGlyAsnValThrPheHisV
    1
151 TACCAAGCAATGTGCCTTTAAAAGAGGTCCTATGGAAAAAACAAAAGGAT 200
    alProSerAsnValProLeuLysGluValLeuTrpLysLysGlnLysAsp
                    20
201 AAAGTTGCAGAACTGGAAAATTCTGAATTCAGAGCTTTCTCATCTTTTAA 250
    LysValAlaGluLeuGluAsnSerGluPheArgAlaPheSerSerPheLy
                                                   50
251 AAATAGGGTTTATTTAGACACTGTGTCAGGTAGCCTCACTATCTACAACT 300
    sAsnArgValTyrLeuAspThrValSerGlySerLeuThrIleTyrAsnL
301 TAACATCATCAGATGAAGATGAGTATGAAATGGAATCGCCAAATATTACT 350
    euThrSerSerAspGluAspGluTyrGluMetGluSerProAsnIleThr
                                             80
351 GATACCATGAAGTTCTTTCTTTATGTGCTTGAGTCTCTTCCATCTCCCAC 400
    AspThrMetLysPhePheLeuTyrValLeuGluSerLeuProSerProTh
                                                  100
401 ACTAACTTGTGCATTGACTAATGGAAGCATTGAAGTCCAATGCATGATAC 450
    rLeuThrCysAlaLeuThrAsnGlySerIleGluValGlnCysMetIleP
451 CAGAGCATTACAACAGCCATCGAGGACTTATAATGTACTCATGGGATTGT 500
    roGluHisTyrAsnSerHisArgGlyLeuIleMetTyrSerTrpAspCys
501 CCTATGGAGCAATGTAAACGTAACTCAACCAGTATATATTTTAAGATGGA 550
    ProMetGluGlnCysLysArgAsnSerThrSerIleTyrPheLysMetGl
                                                  150
551 AAATGATCTTCCACAAAAAATACAGTGTACTCTTAGCAATCCATTATTTA 600
    uAsnAspLeuProGlnLysIleGlnCysThrLeuSerAsnProLeuPheA
601 ATACAACATCATCAATCATTTTGACAACCTGTATCCCAAGCAGCGGTCAT 650
    snThrThrSerSerIleIleLeuThrThrCysIleProSerSerGlyHis
651 TCAAGACACAGATATGCACTTATACCCATACCATTAGCAGTAATTACAAC 700
    SerArgHisArgTyrAlaLeuIleProIleProLeuAlaValIleThrTh
                                                  200
701 ATGTATTGTGCTGTATATGAATGGTATGTATGCTTTTAAAACAAAATAG  750
    rCysIleValLeuTyrMetAsnGlyMetTyrAlaPhe
751 TTTGAAAACTTGCATTGTTTTCCAAAGGTCAGAAAATAGTTTAAGGATGA 800
801 AAATAAAGTTTGAAATTTTAGACATTTGAAAAAAAAAAAAAAAAAAAAA  850
851 AAAAAGCGGCCGC  863
```

FIG. 4
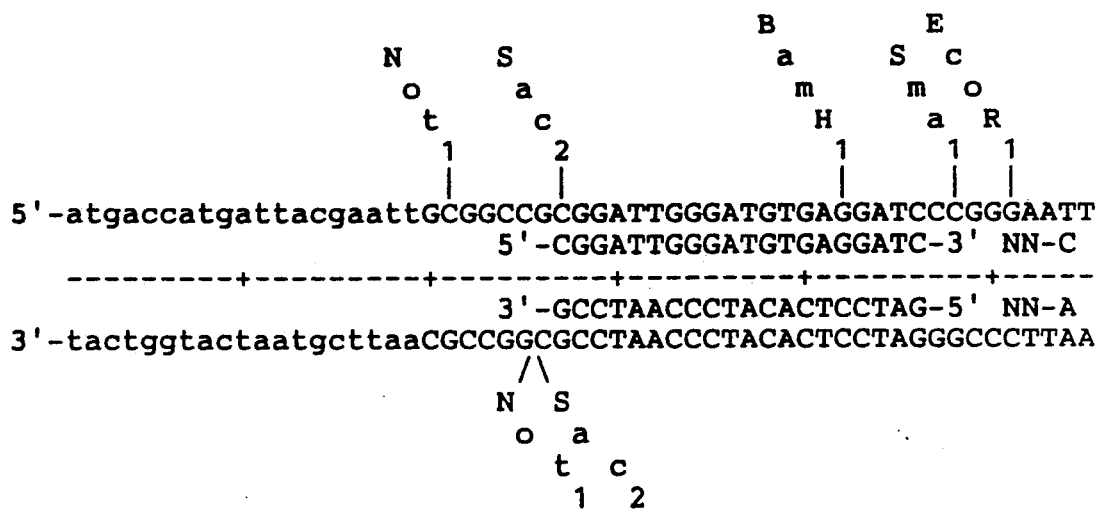
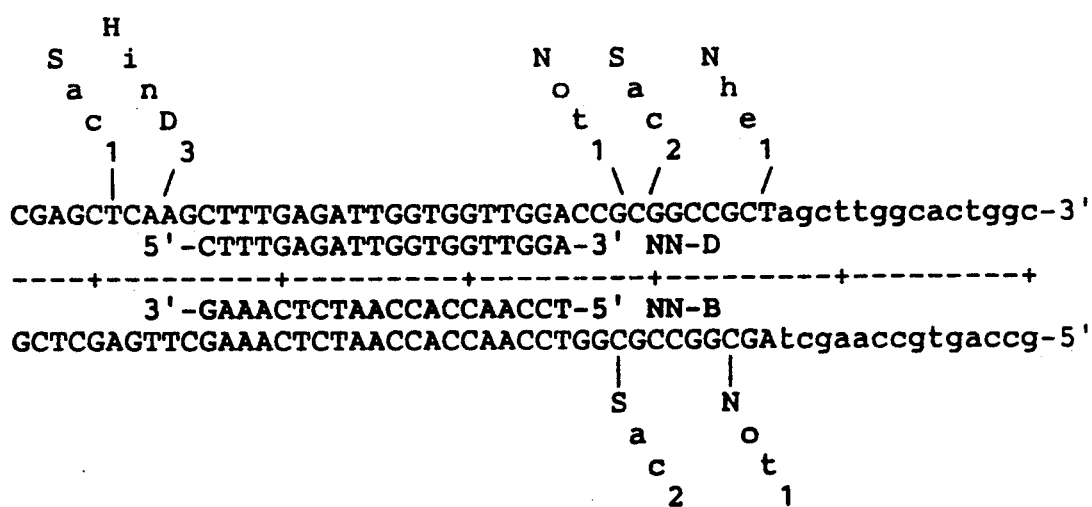

FIG. 6 A

COMPARISON OF HT16 AND P24 cDNAs

```
            M  V  A  G  S  D  A  G  R  A  L  G  V  L
HT16 CGACGAGCCATGGTTGCTGGGAGCGACGCGGGGCGGGCCCTGGGGGTCCT 50
     ||||||||||||||||||||||||||||||||||||||||||||||||||
P24  CGACGAGCCATGGTTGCTGGGAGCGACGCGGGGCGGGCCCTGGGGGTCCT 50
            M  V  A  G  S  D  A  G  R  A  L  G  V  L
      S  V  V  C  L  L  H  C  F  G  F  I  S  C  F  S  Q
HT16 CAGCGTGGTCTGCCTGCTGCACTGCTTTGGTTTCATCAGCTGTTTTTCCC 100
     ||||||||||||||||||||||||||||||||||||||||||||||||||
P24  CAGCGTGGTCTGCCTGCTGCACTGCTTTGGTTTCATCAGCTGTTTTTCCC 100
      S  V  V  C  L  L  H  C  F  G  F  I  S  C  F  S  Q
      Q  I  Y  G  V  V  Y  G  N  V  T  F  H  V  P  S
HT16 AACAAATATATGGTGTTGTGTATGGGAATGTAACTTTCCATGTACCAAGC 150
     ||||||||||||||||||||||||||||||||||||||||||||||||||
P24  AACAAATATATGGTGTTGTGTATGGGAATGTAACTTTCCATGTACCAAGC 150
      Q  I  Y  G  V  V  Y  G  N  V  T  F  H  V  P  S
      N  V  P  L  K  E  V  L  W  K  K  Q  K  D  K  V  A
HT16 AATGTGCCTTTAAAAGAGGTCCTATGGAAAAAACAAAAGGATAAAGTTGC 200
     ||||||||||||||||||||||||||||||||||||||||||||||||||
P24  AATGTGCCTTTAAAAGAGGTCCTATGGAAAAAACAAAAGGATAAAGTTGC 200
      N  V  P  L  K  E  V  L  W  K  K  Q  K  D  K  V  A
      E  L  E  N  S  E  F  R  A  F  S  S  F  K  N  R  V
HT16 AGAACTGGAAAATTCTGAATTCAGAGCTTTCTCATCTTTTAAAAATAGGG 250
     ||||||||||||||||||||||||||||||||||||||||||||||||||
P24  AGAACTGGAAAATTCTGAATTCAGAGCTTTCTCATCTTTTAAAAATAGGG 250
      E  L  E  N  S  E  F  R  A  F  S  S  F  K  N  R  V
      Y  L  D  T  V  S  G  S  L  T  I  Y  N  L  T  S
HT16 TTTATTTAGACACTGTGTCAGGTAGCCTCACTATCTACAACTTAACATCA 300
     ||||||||||||||||||||||||||||||||||||||||||||||||||
P24  TTTATTTAGACACTGTGTCAGGTAGCCTCACTATCTACAACTTAACATCA 300
      Y  L  D  T  V  S  G  S  L  T  I  Y  N  L  T  S
      S  D  E  D  E  Y  E  M  E  S  P  N  I  T  D  T  M
HT16 TCAGATGAAGATGAGTATGAAATGGAATCGCCAAATATTACTGATACCAT 350
     ||||||||||||||||||||||||||||||||||||||||||||||||||
P24  TCAGATGAAGATGAGTATGAAATGGAATCGCCAAATATTACTGATACCAT 350
      S  D  E  D  E  Y  E  M  E  S  P  N  I  T  D  T  M
      K  F  F  L  Y  V  L  E  S  L  P  S  P  T  L  T  C
HT16 GAAGTTCTTTCTTTATGTGCTTGAGTCTCTTCCATCTCCCACACTAACTT 400
     ||||||||||||||||||||||||||||||||||||||||||||||||||
P24  GAAGTTCTTTCTTTATGTGCTTGAGTCTCTTCCATCTCCCACACTAACTT 400
      K  F  F  L  Y  V  L  E  S  L  P  S  P  T  L  T  C
      A  L  T  N  G  S  I  E  V  Q  C  M  I  P  E  H
HT16 GTGCATTGACTAATGGAAGCATTGAAGTCCAATGCATGATACCAGAGCAT 450
     ||||||||||||||||||||||||||||||||||||||||||||||||||
P24  GTGCATTGACTAATGGAAGCATTGAAGTCCAATGCATGATACCAGAGCAT 450
      A  L  T  N  G  S  I  E  V  Q  C  M  I  P  E  H
```

FIG. 6B

```
         Y  N  S  H  R  G  L  I  M  Y  S  W  D  C  P  M  E
HT16 TACAACAGCCATCGAGGACTTATAATGTACTCATGGGATTGTCCTATGGA 500
     ||||||||||||||||||||||||||||||||||||||||||||||||||
P24  TACAACAGCCATCGAGGACTTATAATGTACTCATGGGATTGTCCTATGGA 500
         Y  N  S  H  R  G  L  I  M  Y  S  W  D  C  P  M  E
       Q  C  K  R  N  S  T  S  I  Y  F  K  M  E  N  D  L
HT16 GCAATGTAAACGTAACTCAACCAGTATATATTTTAAGATGGAAAATGATC 550
     ||||||||||||||||||||||||||||||||||||||||||||||||||
P24  GCAATGTAAACGTAACTCAACCAGTATATATTTTAAGATGGAAAATGATC 550
       Q  C  K  R  N  S  T  S  I  Y  F  K  M  E  N  D  L
      P  Q  K  I  Q  C  T  L  S  N  P  L  F  N  T  T
HT16 TTCCACAAAAAATACAGTGTACTCTTAGCAATCCATTATTTAATACAACA 600
     ||||||||||||||||||||||||||||||||||||||||||||||||||
P24  TTCCACAAAAAATACAGTGTACTCTTAGCAATCCATTATTTAATACAACA 600
      P  Q  K  I  Q  C  T  L  S  N  P  L  F  N  T  T
       S  S  I  I  L  T  T  C  I  P  S  S  G  H  S  R  H
HT16 TCATCAATCATTTTGACAACCTGTATCCCAAGCAGCGGTCATTCAAGACA 650
     ||||||||||||||||||||||||||||||||||||||||||||||||||
P24  TCATCAATCATTTTGACAACCTGTATCCCAAGCAGCGGTCATTCAAGACA 650
       S  S  I  I  L  T  T  C  I  P  S  S  G  H  S  R  H
         R  Y  A  L  I  P  I  P  L  A  V  I  T  T  C  I  V
HT16 CAGATATGCACTTATACCCATACCATTAGCAGTAATTACAACATGTATTG 700
     ||||||||||||||||||||||||||||||||||||||||||||||||||
P24  CAGATATGCACTTATACCCATACCATTAGCAGTAATTACAACATGTATTG 700
         R  Y  A  L  I  P  I  P  L  A  V  I  T  T  C  I  V
          L  Y  M  N  G  I  L  K  C  D  R  K  P  D  R  T
HT16 TGCTGTATATGAATGGTATTCTGAAATGTGACAGAAAACCAGACAGAACC 750
     |||||||||||||||||||   |  |  |   |||  ||     |||
P24  TGCTGTATATGAATGGTATGTATGCTTTTTAAAACAAAATAGTTTGAAAA 750
          L  Y  M  N  G  M  Y  A  F
       N  S  N
HT16 AACTCCAATTGATTGGTAACAGAAGATGAAGACAACAGCATAACTAAATT 800
           |   |   |   |   |    ||   |  |    ||      ||
P24  CTTGCATTGTTTTCCAAAGGTCAGAAAATAGTTTAAGGATGAAAATAAAG 800
HT16 ATTTTAAAAACTAAAAAGCCATCTGATTTCTCATTTGAGTATTACAATTT 850
         |·  ||        ||     |        |       |    |·||
P24  TTTGAAATTTTAGACATTTGAAAAAAAAAAAAAAAAAAAAAAAAAAAGCG 850
HT16 TTGAACAACTGTTGGAAATGTAACTTGAAGCAGCTGCTTTAAGAAGAAAT 900
P24  GCCGC     900
HT16 ACCCACTAACAAAGAACAAGCATTAGTTTTGGCTGTCATCAACTTATTAT 950
HT16 ATGACTAGGTGCTTGCTTTTTTGTCAGTAAATTGTTTTTACTGATGATG 1000
HT16 TAGATACTTTTGTAAATAAATGTAAATATGTACACAAGTG    1040
```

DNA SEQUENCES, RECOMBINANT DNA MOLECULES AND PROCESSES FOR PRODUCING PI-LINKED LYMPHOCYTE FUNCTION ASSOCIATED ANTIGEN-3

This invention relates to DNA sequences, recombinant DNA molecules and processes for producing Lymphocyte Function Associated Antigen-3 (PI-Linked form of LFA-3). More particularly, the invention relates to DNA sequences that are characterized in that they code on expression in an appropriate unicellular host for a soluble PI-linked form of LFA-3 or derivatives thereof that bind to CD2, the receptor on the surface of T-lymphocytes. In accordance with this invention, unicellular hosts transformed with these DNA sequences and recombinant DNA molecules containing them may also be employed to produce LFA-3 essentially free of other proteins of human origin. This novel antigen may then be used in the therapeutic and diagnostic compositions and methods of this invention.

BACKGROUND OF THE INVENTION

T-lymphocytes play a major role in the immune response by interacting with target and antigen presenting cells. For example, the T-lymphocyte mediated killing of target cells is a multi-step process involving adhesion of a cytolytic T-lymphocyte to a target cell. And, helper T-lymphocytes initiate the immune response by adhesion to antigen-presenting cells.

These interactions of T-lymphocytes with target and antigen-presenting cells are highly specific and depend on the recognition of an antigen on the target or antigen-presenting cell by one of the many specific antigen receptors on the surface of the T-lymphocyte.

The receptor-antigen interaction of T-lymphocytes and other cells is also facilitated by various T-lymphocyte surface proteins, e.g., the antigen receptor complex CD3(T3) and accessory molecules CD4, LFA-1, CD8, and CD2. It is also dependent on accessory molecules, such as LFA-3, ICAM-1 and MHC that are expressed on the surface of the target or antigen-presenting cells. In fact, it is hypothesized that the accessory molecules on the T-lymphocytes and on the target or antigen-presenting cells interact with each other to mediate intercellular adhesion. Accordingly, these accessory molecules are thought to enhance the efficiency of lymphocyte-antigen-presenting cell and lymphocyte-target cell interactions and to be important in leukocyte-endo-thelial cell interactions and lymphocyte recirculation.

For example, recent studies have suggested that there is a specific interaction between CD2 (a T-lymphocyte accessory molecule) and LFA-3 (a target cell accessory molecule) that mediates T-lymphocyte adhesion to the target cell. This adhesion is essential to the initiation of the T-lymphocyte functional response (M. L. Dustin et al., "Purified Lymphocyte Function-Associated Antigen-3 Binds To CD2 And Mediates T Lymphocyte Adhesion", *J. Exp. Med.*, 165, pp. 677-92 (1987); Springer et al., "The Lymphocyte Function-Associated LFA-1, CD2, and LFA-3 Molecules: Cell Adhesion Receptors Of The Immune System", *Ann. Rev. Immunol.*, 5, pp. 223-52 (1987)). And, monoclonal antibodies to either LFA-3 or CD2 have been shown to inhibit a spectrum of cytolytic T lymphocyte and helper T lymphocyte dependent responses (F. Sanchez-Madrid et al., "Three Distinct Antigens Associated With Human T-Lymphocyte-Mediated Cytolysis: LFA-1, LFA-2, And LFA-3", *Proc. Natl. Acad. Sci. USA*, 79, pp. 7489-93 (1982)).

LFA-3 is found on antigen-presenting cells, and target cells, specifically on monocytes, granulocytes, CTL's, B-lymphoblastoid cells, smooth muscle cells, vascular endothelial cells, and fibroblasts (Springer et al., supra). LFA-3 exists as two distinct cell surface forms (Dustin et al., "Anchoring Mechanisms For LFA-3 Cell Adhesion Glycoprotein At Membrane Surface", *Nature*, 329, pp. 846-848 (1987)). These forms differ mainly by their mechanism of attachment to lipid bilayers of biological membranes. One such anchoring mechanism is via a stretch of hydrophobic amino acids, also referred to as a transmembrane domain, which penetrates the lipid bilayers. cDNA encoding this form of LFA-3, also referred to as an integrated membrane form, has been cloned and sequenced (B. Wallner et al., *J.Exp.Med.*, 166, pp. 923-32 (1987)).

Alternatively, LFA-3 has been reported to insert into the membrane of B-lymphoblastoid cells via a phosphatidylinositol ("PI")-containing glycolipid covalently attached to the C-terminus of the protein (Dustin et al., supra). Membrane insertion of this type was deduced by observing the presence of protein after adding to the cell surface phosphatidylinositol-specific phospholipase. This enzyme releases only the PI-linked form of proteins. It does not affect the integrated membrane form. Thus, the release of LFA-3 in the presence of this enzyme suggests that LFA-3 has a PI-linked form.

The PI-linked form of LFA-3 is believed to be derived from alternative RNA splicing of a gene transcript. It appears to be selectively expressed in different cell types, and during different stages of development than the transmembrane form of LFA-3.

It would be desirable to obtain large amounts of a recombinant PI-linked form of LFA-3, than would be available from purification from natural sources, e.g. lymphoblastoid cells. More desirable would be to obtain large amounts of soluble LFA-3 from a PI-linked form of LFA-3.

SUMMARY OF THE INVENTION

This invention solves these problems. One aspect of this invention is the production of a recombinant PI-linked form of LFA-3. Another aspect of this invention is the production of soluble LFA-3 from a PI-linked form of LFA-3. The latter embodiment is accomplished by expressing DNA sequences encoding a PI-linked form of LFA-3 in cell lines deficient in a PI-linkage attachment mechanism. A still further aspect of this invention is the process of producing a soluble LFA-3 derived from a PI-linked form of LFA-3. This embodiment is accomplished by removing those portions of the DNA sequence encoding the hydrophobic transmembrane region of the PI-linked form of LFA-3.

This invention accomplishes each of these goals by providing DNA sequences coding on expression in an appropriate unicellular host for a PI-linked form of LFA-3 or derivatives thereof.

This invention also provides recombinant DNA molecules containing those DNA sequences and unicellular hosts transformed with them. Those hosts permit the production of large quantities of the PI-linked form of LFA-3, and its derivatives, of this invention for use in a wide variety of therapeutic and diagnostic compositions and methods.

The DNA sequences of this invention are selected from the group consisting of:
(a) the DNA sequence of the DNA insert carried in phage P24; and
(b) DNA sequences which code on expression for a polypeptide coded for on expression by the foregoing DNA sequence.

The DNA sequences of this invention are also selected from derivatives of the DNA insert carried in phage λP24 produced by removing those portions of the DNA sequence encoding the hydrophobic transmembrane region of the PI-linked form of LFA-3.

BRIEF DESCRIPTION OF THE DRAWINGS

FIG. 1 depicts the amino acid sequences of the N-terminal and various peptide fragments of human LFA-3, purified from human erythrocytes using immunoaffinity chromatography.

FIG. 2 depicts two pools of chemically synthesized oligonucleotide DNA probes derived from the amino acid sequence of a human LFA-3 purified from human erythrocytes.

FIG. 3 depicts the DNA sequence of the DNA insert carried in phage P24 and the amino acid sequence deduced therefrom.

FIG. 4 depicts the relevant portions of sequencing plasmid pNN01.

FIG. 5 depicts the nucleotide sequence of probes LF-10, LF-11, NN-A, NN-B, NN-C, and NN-D.

FIGS. 6A and 6B together depict a comparison of the DNA insert carried in phage P24 (and the deduced amino acid sequence) and the DNA insert carried in phage λHT16 (and the deduced amino acid sequence), which codes for an integrated membrane form of LFA-3.

DESCRIPTION OF THE INVENTION

We isolated the DNA sequences of this invention from a λgt10 cDNA library derived from peripheral blood lymphocytes. However, we could also have employed libraries prepared from other cells that express a PI-linked form of LFA-3. These include, for example, monocytes, granulocytes, CTL's, B-lymphoblastoid cells, smooth muscle cells, endothelial cells and fibroblasts. We also could have used a human genomic bank.

For screening this library, we used a series of chemically synthesized anti-sense oligonucleotide DNA probes. We selected these probes from a consideration of the amino acid sequences of various fragments of LFA-3 that we determined using LFA-3 purified from human erythrocytes. These fragments are depicted in FIG. 1. We selected amino acids from various areas that permitted the construction of oligonucleotide probes of minimal degeneracy.

We prepared two pools of probes: LF1 and LF2-5. These pools are depicted in FIG. 2. LF1 is a 32-fold degenerate 20-mer and LF2-5 is a 384-fold degenerate 20-mer. Because of the high degeneracy of this latter pool, we subdivided the pool into four subpools —LF2, LF3, LF4 and LF5 —of 96-fold degeneracy each.

For screening, we hybridized our oligonucleotide probes to our cDNA libraries utilizing a plaque hybridization screening assay. We selected a clone —P24 —hybridizing to one of our probes. And, after isolating and subcloning the cDNA insert of the selected clone, P24, into plasmids, we determined its nucleotide sequence and deduced the amino acid sequence from that nucleotide sequences.

We have depicted in FIG. 3 the nucleotide sequence of the cDNA insert of phage λP24 and the amino acid sequence deduced therefrom. As shown in FIG. 3, this cDNA insert has an open reading frame of 720 bp (240 amino acids), a 17 bp 5' untranslated region and a 93 bp 3' untranslated region. Also present is a transmembrane domain, i.e., from $N_{662}$–$N_{725}$. The 3' untranslated region of P24 contains a poly(A) adenylation site. The P24 cDNA codes for a 240 amino acid protein, including a 28 amino acid signal sequence.

We have depicted in FIGS. 6A and 6B a comparison of the DNA sequences and deduced amino acid sequences of a membrane integrated form of LFA-3 (HT16) and the PI-linked form of LFA-3 of this invention. From this comparison, it is apparent that the last 14 amino acids ($AA_{209}$–$AA_{222}$) including a cytoplasmic domain at the C-terminus of the membrane integrated form of LFA-3 are replaced by 4 different amino acids in the PI-linked form of LFA-3.

The DNA sequences of this invention are selected from the group consisting of:
(a) the DNA sequence of the DNA insert P24 carried in phage P24; and
(b) DNA sequences which code on expression for a polypeptide coded for on expression by the foregoing DNA sequence, e.g., the cDNA sequence depicted in FIG. 3 and contained in deposited clone λP24, may be used, as described below, in a variety of ways in accordance with this invention.

The DNA sequences, portions of them, or synthetic or semi-synthetic copies of them, may be used as a starting material to prepare various mutations. Such mutations may be either silent, i.e., the mutation does not change the amino acid sequence encoded by the mutated codon, or non-silent, i.e., the mutation changes the amino acid sequence encoded by the mutated codon. Both types of mutations may be advantageous in producing or using the LFA-3's of this invention. For example, these mutations may permit higher levels of production, easier purification, or production of secreted shortened or soluble forms of PI-linked forms of LFA-3.

The DNA sequences of this invention are also useful for producing the PI-linked forms of LFA-3, or its derivatives, coded on expression by them in unicellular hosts capable of attaching proteins by PI-linkage, e.g., CHO cells, transformed with those DNA sequences. Preferably, according to a second embodiment of this invention, these DNA sequences may be expressed in a cell line deficient in the PI-linkage attachment mechanism, such as mouse L-cells.e.g., L-M (tk⁻) cells. In this case the LFA-3 may be secreted into the medium in a soluble form. This secreted form of LFA-3 is approximately 3 kd smaller than other forms of LFA-3 retained intracellularly in L-M (tk⁻) cells or extracted from CHO cells. While not wishing to be bound by theory, we believe that the DNA sequences of the present invention produce and secrete a smaller soluble form of LFA-3 because a portion of the transmembrane region is cleaved before or after secretion by cells deficient in a PI-linkage attachment mechanism, and therefore efficient attachment of the PI-linked form of LFA-3 to the cell surface is prevented.

According to another embodiment of this invention DNA sequences encoding a PI-linked form of LFA-3 may be modified as compared to that of FIG. 3 (amino acids −28 to 212) to remove from it portions that code for the hydrophobic transmembrane region, e.g., from about nucleotide 662 to 731, to allow production of soluble LFA-3 protein in any cell transformed with those modified sequences.

As well known in the art, the DNA sequences of this invention are expressed by operatively linking them to an expression control sequence in an appropriate expression vector and employed in that expression vector to transform an appropriate unicellular host.

Such operative linking of a DNA sequence of this invention to an expression control sequence, of course, includes the provision of a translation start signal in the correct reading frame upstream of the DNA sequence. If the particular DNA sequence of this invention being expressed does not begin with a methionine, e.g., a mature PI-linked form of LFA-3 which begins with a phenylalanine, the start signal will result in an additional amino acid —methionine —being located at the N-terminus of the product. While such methionyl-containing-product may be employed directly in the compositions and methods of this invention, it is usually more desirable to remove the methionine before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. However, such in vivo and in vitro methods are well known in the art. Furthermore, the LFA-3's of this invention may include amino acids in addition to the N-terminal methionine at the N-terminus. The LFA-3 may be used with those amino acids or they may be cleaved with the N-terminal methionine before use.

A wide variety of host/expression vector combinations may be employed in expressing the DNA sequences of this invention. Useful expression vectors, for example, may consist of segments of chromosomal, non-chromosomal and synthetic DNA sequences, such as various known derivatives of SV40 and known bacterial plasmids, e.g., plasmids from *E. coli* including col El, pCR1, pBR322, pMB9 and their derivatives, wider host range plasmids, e.g., RP4, phage DNAs, e.g., the numerous derivatives of phage λ, e.g., NM989, and other DNA phages, e.g., M13 and *Filamenteous* single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. In the preferred embodiments of this invention, we employ PBG368,a pBG312-related vector [R. Cate et al., *Cell*, 45, pp. 685-98(1986)].

In addition, any of a wide variety of expression control sequences —sequences that control the expression of a DNA sequence when operatively linked to it —are used in these vectors to express the DNA sequences of this invention. Such useful expression control sequences, include, for example, the early and late promoters of SV40 or the adenovirus, the lac system, the trp system, the TAC or TRC system, the major operator and promoter regions of phage λ, the control regions of fd coat portein, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells or their viruses, and various combinations thereof. For animal cell expression (e.g., L-M (tk−) cells), we prefer to use an expression control sequence derived from the major late promoter of adenovirus 2.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi, such as yeasts, and animal cells, such as CHO and R1.1, B-W and L-M cells, African green monkey cells, such as COS1, COS7, BSC1, BSC40, and BMT10, and human cells and plant cells in tissue culture. For expression of a soluble form of LFA-3, an appropriate host cell is defective in the PI attachment of proteins. We prefer L-M (tk−) cells.

It should of course be understood that not all vectors, expression control sequences and hosts will function equally well to express the DNA sequences of this invention. Neither will all hosts function equally well with the same expression system. However, one of skill in the art may make a selection among these vectors, expression control sequences, and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the system, its controllability, and its compatibility with the particular DNA sequence, of this invention, particularly as regards potential secondary structures. Unicellular hosts should be selected by consideration of their compatibility with the chosen vector, the toxicity of the product coded on expression by the DNA sequences of this invention to them, their secretion characteristics, their ability to fold proteins correctly, their fermentation requirements, and the ease of purification of the products coded on expression by the DNA sequences of this invention.

Within these parameters one of skill in the art may select various vector/expression control system/host combinations that will express the DNA sequences of this invention on fermentation or in large scale animal culture, e.g., mouse cells or CHO cells.

The polypeptides produced on expression of the DNA sequences of this invention may be isolated from the fermentation or animal cell cultures and purified in a variety of ways well known in the art. Such isolation and purification techniques depend on a variety of factors, such as how the product is produced, whether or not it is soluble or insoluble, and whether or not it is secreted from the cell or must be isolated by breaking the cell. One of skill in the art, however, may select the most appropriate isolation and purification techniques without departing from the scope of this invention.

The polypeptides of this invention are useful in compositions and methods to block or to augment the immune responses. For example, they are active in inhibiting cytolytic T-lymphocyte activity by interfering with T-cell interaction with target cells. They have a similar blocking or augmenting effect on the immune response because they interfere with the interaction of helper T-cells and target cells. Furthermore, the compounds of this invention may be used to target specific T cells for lysis and immune suppression or to deliver drugs, such as lymphokines, to the specifically targeted T-cells. More preferably, soluble derivatives of the polypeptides of this invention may be employed to saturate the CD2 sites of T-lymphocytes thus inhibiting T-cell activation. This is plainly of great utility in graft-vs-host disease, in autoimmune diseases, e.g., rheumatoid arthritis, and in preventing allograft rejection. Furthermore, the polypeptides of this invention are preferred over monoclonal antibodies to a PI-linked form of LFA-3 or CD2 because the polypeptides of this invention are less likely to elicit immune responses in humans than are antibodies raised in species other than humans. The therapeutic compositions of this invention typically comprise an immunosuppressant or enhancement effective amount of such polypeptide and a pharmaceutically acceptable carrier. The therapeutic methods of this invention comprise the steps of treating patients in a pharmaceutically acceptable manner with those compositions.

The compositions of this invention for use in these therapies may be in a variety of forms. These include, for example, solid, semi-solid and liquid dosage forms, such as tablets, pills, powders, liquid solutions or suspensions, liposomes, suppositories, injectable and infusable solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

Generally, the pharmaceutical compositions of the present invention may be formulated and administered using methods and compositions similar to those used for other pharmaceutically important polypeptides (e.g., alpha-interferon). Thus, the polypeptides may be stored in lyophilized form, reconstituted with sterile water just prior to administration, and administered by the usual routes of administration such as parenteral, subcutaneous, intravenous or intralesional routes.

The polypeptides of this invention or antibodies against them are also useful in diagnostic compositions and methods to detect T-cell subsets or CD2+cells or to monitor the course of diseases characterized by excess or depleted T-cells, such as autoimmune diseases, graft versus host diseases and allograft rejection. Still further, the polypeptides of this invention may be used to screen for inhibitors of LFA-3 mediated adhesion useful for inhibiting activation of T lymphocytes or T lymphocyte mediated killing of target cells. Such screening techniques are well-known in the art.

Finally, the polypeptides of this invention or antibodies against them are useful in separating B and T cells. For example, when bound to a solid support the polypeptides of this invention or antibodies to them will separate B and T cells.

In order that this invention may be better understood, the following examples are set forth. These examples are for purposes of illustration only, and are not to be construed as limiting the scope of the invention in any manner.

Synthesis Of Oligonucleotide Probes

We obtained a sample of LFA-3 (Dana Farber Cancer Institute, Boston, Massachusetts) previously purified as described by M. Dustin et al., J. Exp. Med., supra and sequenced as described by B. Wallner et al., supra. Next, we chemically synthesized two pools of anti-sense oligonucleotide DNA probes coding for regions from the amino terminal sequence of our sample of LFA-3 characterized by minimal nucleic acid degeneracy (see underscoring in FIG. 1) on an Applied Biosystems 30A DNA synthesizer. For each selected amino acid sequence, we synthesized pools of probes complementary to all possible codons. We synthesized the probes anti-sense to enable hybridization of them to the corresponding sequences in DNA as well as in mRNA. We labelled our oligonucleotide probes using -ATP and polynucleotide kinase (Maxam and Gilbert, Proc. Natl. Acad. Sci, USA, 74, p. 560 (1977)).

As depicted in FIG. 2, the oligonucleotide probe pool LF1 was a 20-mer with 32-fold degeneracy. Probe pool LF2-5, was a 20-mer with 384-fold degeneracy. However, to reduce its degeneracy, we synthesized this pool in four subpools of 96-fold degeneracy each by splitting the degenerate codons for Gly into one of its four possible triplets for each subpool. We then selected the subpool containing the correct sequence from the three pools containing incorrect sequences by hybridization of the individual subpools to Northern blots containing human tonsil mRNA, as described previously (Wallner et al., *Nature*, 320, pp. 77-81 (1986)). Oligonucleotide probe subpool LF2 hybridized to a 1300 nucleotide transcript in human tonsil RNA, which suggested that it contained the correct sequence. Hence, we used it and pool LF1 for screening our various libraries.

Construction Of λgt10 Peripheral Blood Lymphocytes cDNA Library

To prepare our Peripheral Blood Lymphocytes (PBL) DNA library, we processed PBL from leukophoresis #9 through one round of absorption to remove monocytes. We then stimulated the non-adherent cells with IFN-γ 1000 U/ml and 10 μg/ml PHA for 24 h. We isolated RNA from these cells using phenol extraction (Maniatis et al., *Molecular Cloning*, p. 187 (Cold Spring Harbor Laboratory) (1982)) and prepared poly A+mRNA by one round of oligo dT cellulose chromatography. We ethanol precipitated the RNA, dried it in a SPEED-VAC ® vacuum centrifuge and resuspended the RNA in 10 [l $H_2O$ (0.5 μg/μl). We treated the RNA for 10 min at room temperature in $CH_3HgOH$ (5mM final concentration) and β-mercaptoethanol (0.26 M). We then added the methyl mercury treated RNA to 0.1 M Tris-HCl (pH 8.3) at 43° C., 0.01 , $MgCl_2$ 0.01 M DTT, 2 mM Vanadyl complex, 5 μg oligo $dT_{12-18}$, 20 mM KCl, 1 mM dCTP, dGTP, dTTP, 0.5 mM dATP, 2 μCi[α-$^{32}$P]dATP and 30 U 1.5 μl AMV reverse transcriptase (Seikagaku America) in a total volume of 50 μl. We incubated the mixture for 3 min at room temperature and 3 h at 44° C. after which time we stopped the reaction by the addition of 2.5 μl of 0.5 M EDTA.

We extracted the reaction mixture with an equal volume of phenol:chloroform (1:1) and precipitated the aqueous layer two times with 0.2 volume of 10 M $NH_4OAC$, and 2.5 volumes EtOH and dried it under vacuum. The yield of cDNA was 1.5 μg.

We synthesized the second strand according to the methods of Okayama and Berg (*Mol. Cell. Biol.*, 2, p. 161 (1982)) and Gubler and Hoffman (*Gene*, 25, p. 263 (1983)), except that we used the DNA polymerase I large fragment in the synthesis.

We blunt ended the double-stranded cDNA by resuspending the DNA in 80 μl TA buffer (0.033 M Tris Acetate (pH 7.8); 0.066 M KAcetate; 0.01M MgAcetate; 0.001M DTT; 50 μg/ml BSA), 5 μg RNase A, 4 units RNase H, 50 μM α AND , 8 units *E.coli* ligase, 0.3125 mM dATP, dCTP, dGTP, and dTTP, 12 units T4 polymerase and incubated the reaction mixture for 90 min at 37° C., added 1/20 volume of 0.5M EDTA, and extracted with phenol: chloroform. We chromatographed the aqueous layer on a cross-linked dextran gel filtration column (SEPHADEX G-150, Pharmacia, Piscataway, NJ) in 0.01M Tris-HCl (pH 7.5), 0.1 M NaCl, 0.001 M EDTA and collected the lead peak containing the double-stranded cDNA and ethanol precipitated it. Yield: 605 μg cDNA.

We ligated the double-stranded cDNA to linker 35/36

```
5'AATTCGAGCTCGAGCGCGGCCGC3'
3'     GCTCGAGCTCGCGCCGGCG5'
``` using standard procedures. We then size selected the cDNA for 800 bp and longer fragments on a gel filtration column of dextran cross-linked with acrylamide (SEPHACRYL S-500, Pharmacia, Piscataway, NJ) and ligated it to EcoRI digested λgt10. We packaged aliquots of the ligation reaction using a commercially available λ phage packaging extract (GIGAPAK, Stratagene, La Jolla, CA) according to the manufacturer's protocol. We used the packaged phage to infect *E.coli* BNN102 cells and plated the cells for amplification. The resulting library contained $1.125 \times 10^6$ independent recombinants.

Screening Of The Libraries

We screened the PBL cDNA library prepared above with our labelled oligonucleotide probe LF1 using the plaque hybridization screening technique of Benton and Davis (*Science*, 196, p. 180 (1977)).

We pelleted an overnight culture of BNN102 cells in L broth and 0.2maltose and resuspended it in an equal volume of SM buffer (50 mM Tris-HCl (pH 7.5), 100 mM NaCl, 10 mM MgSO4, and 0.01% gelatin). Thereafter, we preadsorbed 9 ml of cells with $1.5 \times 10^6$ phage particles at room temperature for 15 minutes and plated them on 30 LB Mg plates.

After incubation at 37° C. for 8 hours, we adsorbed plaques onto filters from the plates and lysed the filters by placing them onto a pool of 0.5 N NaOH/1.5 M NaCl for 5 minutes, and then submerged them for 5 min in the same buffer. We neutralized the filters by submerging them in 0.5 M Tris-HCl (pH 7.4), 1.5 M NaCl, two times for 5 minutes each, and rinsed them for 2 minutes in 1 M NH4OAc, air dried the filters, and baked them for 2 hours at 80° C.

We prehybridized and hybridized the filters to oligonuoleotide probe LF1 in 0.2% polyvinylpyrolidone, 0.2% FICOLL (MW 400,000), 0.2% bovine serum albumin, 0.05 M Tris-HCl (pH 7.5), 1 M sodium chloride, 0.1% sodium pyrophosphate, 1% SDS, and 10% dextran sulfate (MW 500,000). We detected the hybridizing λ-cDNA sequences by autoradiography.

We initially selected 26 positive phages from the PBL library and rescreened these clones and plaque purified them at lower density using the same probe.

Sequencing Of The P24 cDNA Clone

We characterized the cDNA from a clone, P24, screened above by DNA sequencing analysis. We subcloned the NotI digested DNA from clone λP24 into vector pNN01 to give p24 and to facilitate sequence analysis.* The entire insert of λP24 is contained on a single NotI fragment. For subcloning, we used the vector's EcoRI site or SmaI site employing techniques in common use.

We determined the DNA sequences of our subclones largely by the, method of Maxam and Gilbert (*Meth. Enzymology*, 65 pp. 499–560) 1980). However, for some fragments, we used the related procedure of Church and Gilbert (*Proc. Natl. Acad. Sci. USA*, 81, p. 1991 (1984)). The structure of pNN01 enables sequencing, by the Church-Gilbert approach, of the ends of an inserted fragment using NotI digestion and four 20-nucleotide long probes: NN-A, NN-B, NN-C and NN-D. See FIG. 5.

FIG. 3 shows the DNA sequence of the cDNA insert of phage λP24. It also depicts the amino acid sequence deduced therefrom.

Determination Of Linkage Form Of LFA-3 From P24 cDNA

We decided to characterize the linkage form of LFA-3 coded for by P24 cDNA. We choose the R1.1 cell line because it is known to express surface antigens that are attached to the membrane by a PI linkage.

We incubated $5 \times 10^6$ cells of clones P24/R1.1, HT16/R1.1 (an R1.1 cell line transfected with cDNA coding for a membrane integrated form of LFA-3 (see, B. Wallner et al., supra)) and R1.1 cells with 0.5 μl of phosphatidylinositol-specific phospholipase C (PIPLC) at 37° C. for 1 hour. It is known that PIPLC upon incubation releases PI-linked proteins from the cell surface, while it has no effect on proteins attached to the cell surface by other mechanisms such as membrane integrated proteins (M. Low, Biochem. J., 244, p. 1 (1987)).

We determined the amount of LFA-3 released from the cell surface of P24/R1.1 or HT16/R1.1 by the decrease of surface fluorescence assayed on FACS. We found that incubation of P24/R1.1 cells with PIPLC resulted in the release of 95% of surface LFA-3 while PIPLC did not have any effect on the fluorescence of R1.1 cells or HT16/R1.1 cells. This indicates that P24 cDNA codes for the PI-linked form of LFA-3.

Adhesion Of a PI-linked form of LFA-3 From P24/R1.1 To Other Cells

We next tested whether a PI-linked form of LFA-3 from P24 cDNA as expressed in R1.1 cells would mediate adherence of P24/R1.1 to other cells. We tested this by rosetting analysis with L-cells expressing CD2 cDNA (L114). We grew control L cells and L114 (CD2 transfected) cells, in a 9.6 cm² well of a 6 well tissue culture plate at a cell density of $3 \times 10^5$ cells per well. After washing the wells twice with Roswell Park Memorial Institute (RPMI 1060) medium to remove cell debris and dead cells, $1.5 \times 10^7$ P24/R1.1 or R1.1 cells as a control were added per well. Plates were spun at 400 rpm for 2 minutes in a Sorvall Centrifuge at 4° C. After the cells were incubated at 4° C. for 2 hours, the wells were washed with RPMI 1060 medium to remove excess P24/R1.1 or R1.1 cells. P24/R1.1 cells rosetted with the L114 cells as determined under the microscope. We observed rosetting of P24/R1.1 with L114 cells but not with the untransfected control cells. This rosetting could be inhibited with MAb to LFA-3 (TS2/9) or MAb to CD2 (TS2/18). This indicates that a PI-linked form of LFA-3 is expressed on cell surface of R1.1 cells in a conformation that allows interaction with recombinant CD2 expressed on mouse L-cells. P24/R1.1 cells or untransfected R1.1 cells do not rosette with untransfected mouse L-cells, indicating the specificity of these cellular interactions.

Expression Of PI-linked Form Of LFA-3 From P24 cDNA In CHO cells

We inserted a Klenow blunt-ended NotI PI-linked form of LFA-3 cDNA fragment of p24 into a blunt-ended SalI site of plasmid pJOD-s to give pJOD-s-LFA3P24.

Vector pJOD-s has been deposited in the In Vitro International, Inc. Culture Collection, 611 P. Hammonds Ferry Rd., Linthicum, Maryland, 21090 on July 22, 1988 and has been assigned accession number 10179. This deposit was transferred to the American Type Culture collection, Rockville, Maryland, on Jun. 20, 1991 and assigned accession number ATCC 68787.

We next linearized pJOD-s-LFA3P24 with PvuI for transfection of CHO cells. We incubated 10μg of PvuI linearized DNA with 0.125 M $CaCl_2$ in TE and 1×HEBS (137 mM NaCl, 5mM KCl, 0.0030 M $Na_2HPO_4$, 0.7 $H_2O$, 6mM Dextrose, 20 mM Hepes (pH 7.1)) at room temperature for 20 minutes. DNA was added to cells in alpha+-MEM medium and incubated at 37° C. for 4 hours. After removing the medium, cells were incubated at room temperature for 4 minutes in alpha+-MEM +10% glycerol. Cells were rinsed with medium and grown for 2 days in alpha+-MEM, then transferred to selective medium (alpha−-MEM).

We determined expression of a PI-linked form of LFA-3 by FACS analysis. To analyze by FACS, $1 \times 10^6$ cells per each P24-CHO methotrexate clone and control CHO cells were removed from the tissue culture dishes by incubation with Hank's BSS buffer, 0.5 M EDTA at 4° C. for 15 minutes. The detached cells were then pelleted, resuspended in 50 μl of PBN buffer (1×PBS,0.5% BSA, 0.1% sodium azide) and incubated with 100 μl of MAb TS2/9 (1.2 mg/ml) (a gift of Tim Springer) on ice for 45 minutes. We next washed the cells two times with 1 ml PBN buffer and pelleted by centrifugation. The cell pellets were resuspended in 100μl of a 1:50 dilution of FCI (Fluorescein Conjugated Affinity Purified F (ab')$_2$ Fragment Sheep Anti-Mouse IgG (Cappel, Biomedical, Pennsylvania)) in PBN buffer and incubated on ice for 30 minutes. Cells were pelleted by centrifugation and excess FCI was removed by resuspending the cell pellets twice in 1 ml PBN buffer. We then resuspended the cells in 800 μl of 1×PBS and determined the fluorescence intensity on FACS. We observed five clones showed between 5 to 50 fold higher fluorescence than control CHO cells.

Expression Of A PI-linked Form Of LFA-3 From P24 cDNA In R1.1 cells

We used expression vector pBG24 derived from expression vector pBG312. pBG24 was constructed by digesting plasmid p24 DNA with NotI and blunt-ended with Klenow. We next isolated a 860 bp NotI fragment of p24 followed by ligation with an EcoRI linearized, blunt-ended expression vector PBG368. PBG368 was constructed as follows. Animal expression vector pBG312 (described R. Cate et al., Cell, 45, pp. 685-98 (1986) was digested with EcoRI and BglII to delete one of each of the two EcoRI and the two BglII restriction sites (the EcoRI site at position 0 and the BglII site located at approximately position 900). A bacterial strain (pBG312.hmis/JA221) harboring plasmid pBG312 bearing a DNA insert coding for human Mullerian inhibiting substance was deposited with In Vitro International, Inc., Linthicum, Maryland, on Oct. 23, 1985, assigned accession number IVI-10089 and has been publicly available since Sep. 10. 1991. This deposit was transferred to the American Type Culture Collection, Rockville, Maryland on Jun. 20, 1991, an dis available from there under accession number ATCC 68813.

90 μg DNA of pBG24 was linearized with NruI, and cotransfected with 10 μg of NruI linearized pTCF DNA (F. Grosveld et al., Nucleic Acid Res., 10, p. 6715 (1982)) and 300 μg sonicated salmon sperm DNA by DNA electroporation using a BIORAD (Richmond, California) GENE PULSER ® set at 0.29 kV with capacitance set at 960 μFd. We selected for transfection R1.1 cells in RPMI 1060 medium +1 mg/ml G418. We selected single clones after limiting dilutions to $10^3$ cells per well in a 96 well dish in selective medium. Eight clones, resistant to G418, were assayed for a PI-linked form of LFA-3 expression by FACS analysis as described above. All eight P24/R1.1 clones expressed PI-linked form of LFA-3 at a level 10 to 1000 fold above R1.1 control cells.

Expression Of A PI-linked Form Of LFA-3 P24 cDNA In L Cells

To express our P24 cDNA in mouse L cells, we cotransfected 90 μg of plasmid pBG24 DNA ,as described above, that was linearized with NruI with 10μg plasmid pOPF DNA carrying a thymidine kinase gene (tk) (Grosveld et al., supra), linearized with ScaI into $1 \times 10^7$ L-M (tk-) cells (C. P. Terhorst, J. Immun., 131, p. 2032 (1983)) by electroporation as described above. We selected for transfected cells by tk expression by growing them in DMEM +HAT at cell densities of $1 \times 10^5$ cells per 100 mm plate. Clones were picked and expanded to $5 \times 10^5$ cells per 100 mm dish to assay for expression of a PI-linked form of LFA-3 by FACS analysis as described above. We observed some expression at levels above control cells, although 70% of the PI-linked form of LFA-3 was secreted into the medium as discussed below.

Secretion Of LFA-3 From P24/L Cells

We further wanted to test whether P24/L cells secrete LFA-3 because this mouse L cell line—L-M(tk−) —is known to be deficient in a PI linkage attachment mechanism. P24/L cells were metabolically labeled with $^{35}$S-met and the 35S-labelled PI-linked form of LFA-3 was precipitated from the medium with MAb TS2/9 (a gift of Tim Springer) as follows. 3 $\times 10^5$ P24/L, HT16/L (B. Wallner et al., supra) or L(tk-) cells were plated in 1 well each of a 6 well cell culture plate, grown overnight in DMEM-HAT complete medium (DMEM +HAT +10% FCS +glutamine). Wells were then rinsed with 1x Minimal Essential Medium Eagle (modified) methionine free (MEM). For $^{35}$S met labeling, we added 1.5 ml of MEM medium (methionine free), plus glutamine, 2.5% complete DMEM and 225 μCi $^{35}$S met (New England Nuclear, Delaware, 1135 mCi/μm) to each well and incubated at 37° C. for 18 hours. To 0.7 ml of medium 10 μl of MAb TS2/9 coupled to agarose was added, and the mixture rocked at 4° C. overnight. To each well we added 300 μl of DOC buffer (20 mM Tris (pH 7.3), 50mM sodium chloride, 0.5% deoxycholate, 0.5% cells off the plates, transferred to Eppendorf tubes, vortexed and centrifuged for 15 minutes at room temperature. To 100 µl of the supernatant, 10 µl of MAb TS2/9 coupled to agarose was added and incubated overnight at 4° C. with rocking. The TS2/9-agarose $^{35}$S-LFA-3 complex was pelleted by centrifugation, washed three times with 1 ml of DOC buffer, and resuspended in 50 µl SDS-loading buffer. $^{35}$S-LFA-3 (PI-linked form) was dissociated from TS2/9-agarose by heating the complex to 65° C for 10 minutes. The TS2/9 agarose was precipitated by centrifugation and 25 µl of the supernatant was electrophoresed on a reducing SDS-polyacrylamide gel. We observed precipitation of the 55 kd $^{35}$S-labelled protein with MAb TS2/9 only from the medium of P24/L cells and not from the medium of L-M(tk−) control cells.

We determined by SDS-PAGE that the $^{35}$S-LFA-3 labeled LFA-3, secreted from P24/L cells is approximately 3 kd smaller than the $^{35}$S-labelled LFA-3 retained intracellularly in P24/L cells or HT16/L cells. This indicates that a portion or all of the hydrophobic potential transmembrane region is removed before secretion, which prevents the efficient integration of a PI-linked form of LFA-3 into the cell surface membrane.

We deposited the following plasmid carrying a PI-linked form of LFA-3 cDNA sequence of this invention in the In Vitro International, Inc. Culture Collection in Linthicum, Maryland, on Jul. 22, 1988:

The plasmid has been assigned accession number IVI-10180. This deposit was transferred to the American Type Culture Collection, ockville, Maryland, on Jun. 20, 1991 and has been assigned accession number ATC 68788.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which we have presented by way of example.

We claim:

1. A DNA molecule with a DNA sequence selected from the group consisting of:
   (a) the DNA sequence of the DNA insert carried in phage λP24; and
   (b) DNA sequences which are degenerate to the foregoing DNA sequence.

2. A DNA molecule with a DNA sequence selected from the group consisting of a DNA sequence of the formula $N_{1-830}$ of FIG. 3, a DNA sequence of the formula $N_{18-830}$ of FIG. 3, a DNA sequence of the formula $N_{102-830}$ of FIG. 3 and DNA sequences which are degenerate to any of the foregoing DNA sequences.

3. A DNA molecule with a DNA sequence selected from the group consisting of a DNA sequence of the formula $N_{1-653}$-$N_{738-830}$ of FIG. 3, a DNA sequence of the formula $N_{102-653}$-$N_{738-830}$ of FIG. 3, a DNA sequence of the formula $N_{1-662}$-$N_{738-830}$ of FIG. 3, a DNA sequence of the formula $N_{102-662}$-$N_{738-830}$ of FIG. 3, a DNA sequence of the formula $N_{1-638}$-$N_{738-830}$ of FIG. 3, a DNA sequence of the formula $N_{102-638}$-$N_{738-830}$ of FIG. 3, a DNA sequence of the formula $N_{1-701}$-$N_{738-830}$ of FIG. 3, a DNA sequence of the formula $N_{102-701}$-$N_{738-830}$ of FIG. 3, and DNA sequences that are degenerate to any of the foregoing DNA sequences.

4. A recombinant DNA molecule comprising an isolated DNA molecule according to claim 1 or 2, said DNA molecule being operatively linked to an expression control sequence in said recombinant DNA molecule.

5. A recombinant DNA molecule comprising a DNA molecule of claim 3, said DNA molecule being operatively linked to an expression control sequence in said recombinant DNA molecule.

6. The recombinant DNA molecule according to claim 4, wherein the molecule is pJOD-s-LFA3P24.

7. A unicellular host transformed with a recombinant DNA molecule according to claim 4.

8. A unicellular host transformed with a recombinant DNA molecule according to claim 5.

9. A unicellular host transformed with a recombinant DNA molecule according to claim 4 wherein said host is selected from the group consisting of CHO cells and R1.1 cells.

10. A unicellular host transformed with a recombinant DNA molecule according to claim 4 wherein said host is L-M(tk−).

11. The recombinant DNA molecule according to claim 4, wherein side expression control sequence is selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase or other gylcolytic enzymes, the promoters of acid phosphatase and the promoters of the yeast α-mating factors.

12. The recombinant DNA molecule according to claim 5, wherein said expression control sequence is selected from the group consisting of the early or late promoters of SV40 or adenvirus, the lac system, the trp system, the TAC system, the TRC system, the major operator and promoter regions of pahge λ, the control regions of fd coat protein, the promoter for 3-phosphoglycerate kinase or other glycolytic enzymes, the promoters of acid phosphatase and the promoters of the yeast α-mating factors.

13. A unicellular host transformed with a recombinant DNA molecule according to claim 4, wherein said host is selected from the group consisting of strains of E.coli, Pseudomonas, Bacillus, Streptomyces, yeast, fungi, animal cells, plant cells and human cells in tissue culture.

14. A unicellular host transformed with a recombinant DNA molecule according to claim 4, wherein said unicellular host secretes a soluble from of LFA-3 when transformed with the DNA insert carried in phage λP24.

15. A unicellar host transformed with a recombinant DNA molecule according to claim 4, wherein cell surface proteins of said unicellular host are resistant to phosphatidylinositol-specific phospholipase C treatment.

* * * * *